United States Patent [19]

Blackmore et al.

[11] Patent Number: 5,542,437

[45] Date of Patent: Aug. 6, 1996

[54] EYELID WEIGHTING SYSTEM

[76] Inventors: John M. Blackmore, 620 East View Way, Redwood City, Calif. 94062; Richard P. Jobe, 26985 Orchard Hill La., Los Altos Hills, Calif. 54022

[21] Appl. No.: 271,092

[22] Filed: Jul. 6, 1994

[51] Int. Cl.$^6$ ................................................. A61B 19/00
[52] U.S. Cl. ............................................. 128/899; 623/4
[58] Field of Search ...................... 128/897–99; 623/4; 606/204.25, 204.35

[56] References Cited

PUBLICATIONS

Barclay, et al., "Restoration of Movement to the Upper Eyelid in Facial Palsy", British Journal of Plastic Surgery 22, 1969, pp. 257–261.

Jobe, "A Technique for Lid Loading in the Management of Lagophthalmos of Facial Palsy", Plastic and Reconstructive Surgery, vol. 53 No. 1, 1974, pp. 29–32.

Seiff, et al., "Pretarsal Fixation of Gold Weights in Facial Nerve Palsy", Ophthalmic Plastic and Reconstructive Surgery, vol. 5 No. 2, 1989, pp. 104–109.

Kartush, et al., "Early Gold Weight Eyelid Implantation for Facial Paralysis", Otolaryngology—Head and Neck Surgery, vol. 103 No. 6, Dec. 1990, pp. 1016–1023.

Sobol, et al., "Early Gold Weight Lid Implant for Rehabilitation of Faulty Eyelid Closure with Facial Paralysis; an Alternative to Tarsorrhaphy", Head and Neck Surgery, Mar./Apr. 1990, pp. 149–153.

Petruzzelli, et al., "Bell's Palsy, a Diagnosis of Exclusion", Postgraduate medicine vol. 90 No. 2, Aug. 1991, pp. 115–127.

Seiff, et al., "Management of Ophthalmic Complications of Facial Nerve Palsy", Otolaryngologic Clinics of North America, vol. 25 No. 3, Jun. 1992, pp. 669–690.

Townsend, "Eyelid Reanimation for the Treatment of Paralytic Lagophthalmos: Historical Perspectives and Current Applications of the Gold Weight Implant", Ophthalmic Plastic & Reconstructive Surgery, vol. 8 No. 3, 1992 pp. 196–201.

Muller–Jensen, et al., "Zur Operativen und Konservativen Behandlung des Lagophthalmus (Fazialisparese)", Ophthamologe (1993) 90:27–30, English Summary, p. 30.

*Primary Examiner*—Angela D. Sykes
*Assistant Examiner*—John P. Lacyk
*Attorney, Agent, or Firm*—Flehr, Hohbach, Test, Albritton & Herbert

[57] ABSTRACT

An eyelid weighting system for the treatment of lagophthalmos. The weighting system includes a weight body having a concave first surface with a radius of curvature substantially conforming to the curvature of the eyeball and a second surface spaced from the first surface. First and second major edges join the first and second surfaces and a pair of side edges extend between the first and second major edges.

5 Claims, 3 Drawing Sheets

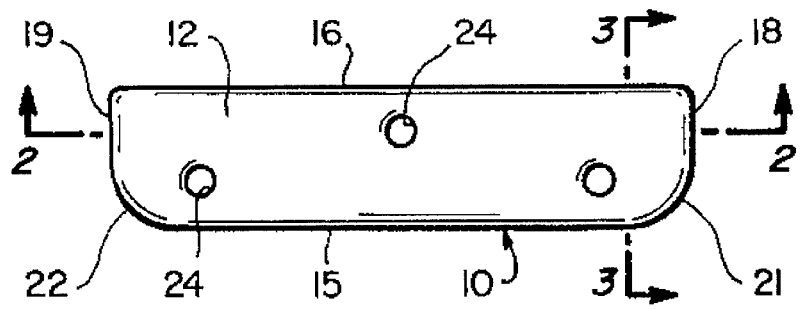
FIG_1
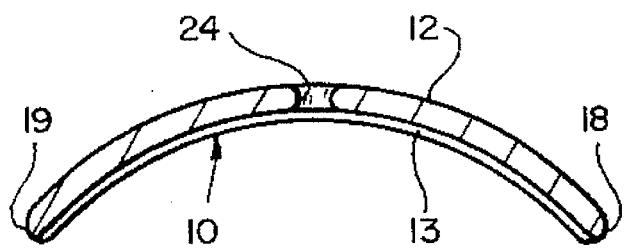
FIG_2
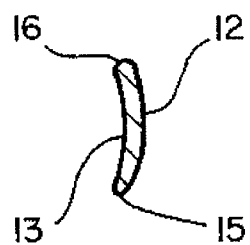
FIG_3
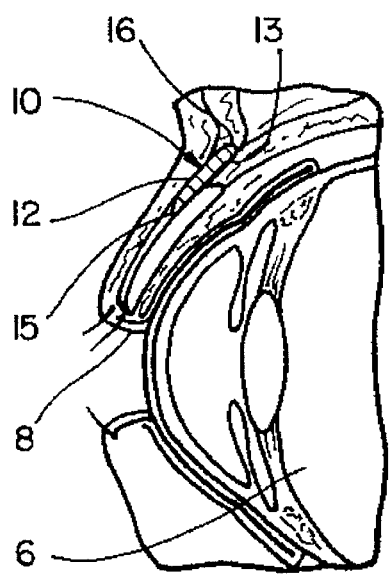
FIG_4A
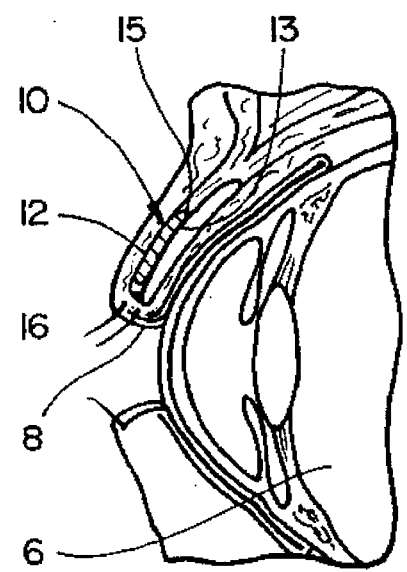
FIG_4B

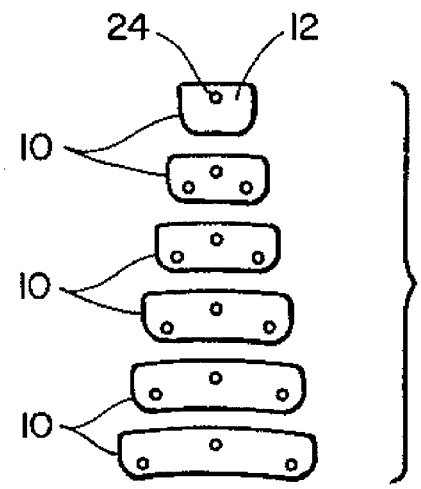
FIG_5
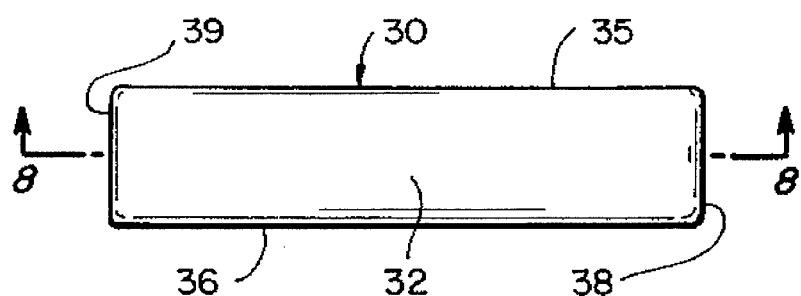
FIG_6
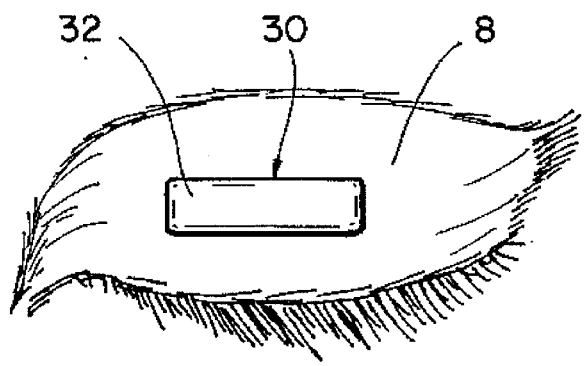
FIG_7

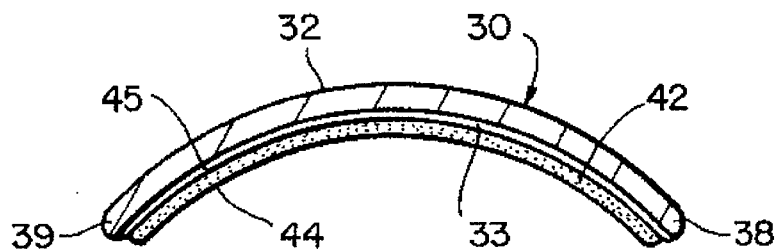
FIG_8
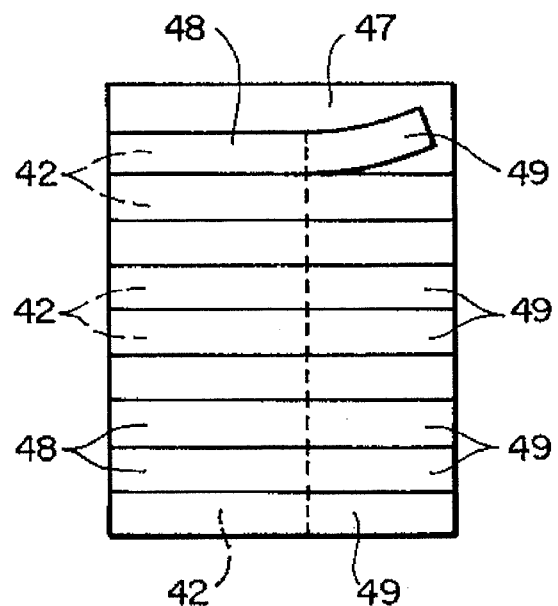
FIG_9
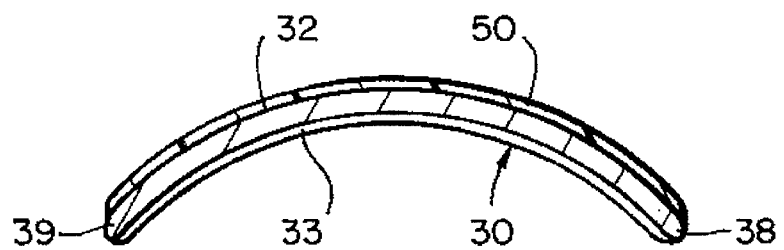
FIG_10

EYELID WEIGHTING SYSTEM

BRIEF DESCRIPTION OF THE INVENTION

This invention relates in general to a system for the treatment of lagophthalmos and, more particularly, to an eyelid weighting device for improving eyelid closure.

BACKGROUND OF THE INVENTION

Facial paralysis may arise from injury to the facial nerve as a result of Bell's Palsy, trauma, surgical damage, tumors, infections and various other conditions. The paralysis may be a temporary or permanent condition. Patients suffering from facial paralysis may experience such symptoms as lagophthalmos, asymmetry or distortion of facial expression, drooling, speech difficulty and the like. Lagophthalmos (the inability to fully close the eye) leaves the eye exposed and may result in serious damage or injury to the eye. For example, excessive exposure of the eye may cause pain, discomfort, ocular irritation, conjunctival desiccation, conjunctivitis, epiphora and the like and may lead to the development of keratitis, corneal abrasion or ulceration, and even blindness. Thus, a critical consideration in the treatment of patients with facial paralysis is the protection of the eye.

Depending upon the ability of the patient to partially close the eye, the eye may be protected by lubricating the eye with ophthalmic drops, ointments protective moisture chambers, occlusive bubbles and the like. However, repeatedly lubricating the eye is cumbersome for the patient, often causes obscured vision and discomfort, and may not sufficiently protect the eye. Surgical procedures, such as tarsorrhaphy (suturing the eyelids together) and implanting various prosthetic devices in the eyelids, may be used to improve eyelid closure and reduce exposure of the eye. Suturing the eyelids together provides some protection for the eye but generally prevents active eyelid closure, restricts peripheral vision and may be cosmetically unattractive to the patient. Moreover, the lids may be deformed when the procedure is reversed, particularly if the procedure involves the use of permanent sutures and the excision of soft tissue. Prosthetic devices such as tantalum gauze mesh, silicone rubber elastic strips, stainless steel springs and magnets implanted in the upper and lower lids provide some amount of active eyelid closure. However, the prosthetic devices have been associated with a significant occurrence of infection and extrusion of the prosthetic device from the eyelid. Furthermore, the procedures used to implant the prosthetic device may be difficult to master and a second procedure may be required to adjust the placement or fixation of the prosthetic device.

Gold weight implants have also been used in the surgical treatment of lagophthalmos. The gold weights are implanted in the upper eyelid and secured to either the tarsal plate, orbital septum or levator aponeurosis. When the levator muscle is relaxed, the upper eyelid is lowered by the force of gravity, substantially closing the eye. The gold implants are available in several weights to provide the required amount of assistance for the eyelid to close. The implants are generally formed in the shape of a cylindrical arc and have a radius which conforms to the curvature of the eye. One type of gold weight implant is shaped to conform to the curvature of the cornea; however, the steeper inclination of the implant concentrates the weight of the implant on a small area of the eye, often inducing more astigmatism than other prosthetic devices. Because of the steep inclination, the implant is also more likely to extrude from the eyelid.

The optimum weight required for eyelid closure is determined by temporarily attaching the implant to the exterior of the eyelid with rubber adhesive, dermatome glue, tincture of benzoin, adhesive tape and the like. The effect of the implant on the eyelid as the patient looks up and down is observed, and the process is repeated with an implant having a different weight as necessary. When the patient is looking straight ahead, the gold weight preferably holds the lid about one millimeter lower than the normal eyelid. The selected gold implants are then removed from the eyelid, sterilized and implanted in the upper lid. The implant is secured to either the tarsal plate, orbital septum or levator aponeurosis depending upon whether pretarsal or septal placement is desired. If facial paralysis is a temporary condition, the gold weight implant may be easily removed once eyelid function is regained.

OBJECTS AND SUMMARY OF THE INVENTION

It is a primary object of this invention to provide an eyelid weighting system for the treatment of lagophthalmos which includes an eyelid weighting device that conforms to the shape of the eyeball or globe.

It is another object of this invention to provide an eyelid weighting system having a plurality of reusable sizing weights for determining the weight required for optimum eyelid closure.

It is yet another object of this invention to provide an eyelid weighting device with a broad spherical radius of curvature to distribute the weight of the device over the eyeball, thereby minimizing any induced astigmatism.

It is an additional object of this invention to provide an eyelid weighting system which may be worn on the external eyelid for prolonged periods of time to treat temporary lagophthalmos resulting from Bell's Palsy.

It is another object of this invention to provide an eyelid weighting device which may be applied to the eyelid exterior for an extended period of time to monitor the effect of the weight on the lid.

It is yet another object of this invention to provide such an eyelid weighting device which is colored to blend with the color of the skin.

It is a further object of the invention to provide an eyelid weighting device with a colored coating representing the weight of the device.

It is another object of the invention to provide an eyelid weighting system having adhesive strips for safely and securely attaching the weighting device to the exterior of the eyelid and for easily removing the weighting device from the eyelid.

A more general object of this invention is to provide an eyelid weighting system which may be efficiently used by the physician and which facilitates eyelid closure, minimizes discomfort and enhances the facial appearance of the patient.

In summary, the present invention provides an eyelid weighting system which is particularly suitable for the treatment of permanent or temporary lagophthalmos. The eyelid weighting system includes a weight body having a concave inner surface shaped to conform to the eye and an outer surface, first and second major edges joining the inner and outer surfaces and a pair of side edges extending between the major edges. The curvature of the concave surface substantially conforms to the curvature of the eye.

In one modification of the invention, the weighting device is adapted to be implanted in the eyelid. To reduce the profile of the weighting device in the lid, the first major edge is preferably tapered to reduce the thickness of the weighting device along the first major edge. The first major edge also preferably has opposed contoured ends. The weighting device optionally includes at least one aperture for fixation of the device to the eyelid.

In another modification of the invention, the weighting device is formed for attachment to the exterior of the lid. The weighting device optionally includes a colored layer on at least the outer surface which blends with the coloring of the eyelid. Alternatively, the colored layer may be coded to identify the weight of the device. The device is secured to the eyelid using attachment means as for example an adhesive strip.

Additional objects and features of the invention will be more readily apparent from the following detailed description and appended claims when taken in conjunction with the drawings.

BRIEF DESCRIPTION OF THE DRAWINGS

FIG. 1 is a top plan view of an eyelid weighting device in accordance with this invention.

FIG. 2 is a cross-sectional view taken along line 2—2 in FIG. 1.

FIG. 3 is a cross-sectional view taken along line 3—3 in FIG. 1.

FIGS. 4A and 4B are schematic views showing the placement of the weighting device when implanted in the eyelid.

FIG. 5 is a schematic view showing a set of different sized weighting devices.

FIG. 6 is a top plan view of an eyelid weighting device in accordance with another embodiment of this invention.

FIG. 7 is a schematic view showing the weighting device of FIG. 6 attached to the outer skin of the eyelid.

FIG. 8 is a cross-sectional view taken along line 8—8 in FIG. 6, shown with an adhesive strip adhered to the concave inner surface.

FIG. 9 is a top plan view of a plurality of adhesive strips.

FIG. 10 is a cross-sectional view of the eyelid weighting device of another embodiment in accordance with the invention.

DETAILED DESCRIPTION OF THE INVENTION

Reference will now be made in detail to the preferred embodiment of the invention, which is illustrated in the accompanying figures. Turning now to the drawings, wherein like components are designated by like reference numerals throughout the various figures, attention is directed to FIGS. 1 to 5.

An eyelid weighting device or implant 10 incorporating the invention is shown in FIG. 1. The implant 10, which is particularly suitable for the treatment of lagophthalmus, has an outer surface 12 and a concave inner surface 13. The concave surface 13 has a substantially spherical curvature which conforms to the curvature of the eyeball or globe 6. The outer surface 12 preferably follows the general shape of the inner surface 13 as shown to reduce the visibility of the implant 10 in the eyelid. However, the outer surface 12 may be formed with other shapes. In the preferred form, the concave surface 13 has a radius of curvature of between approximately 11.5 to 13.5 mm, for example approximately 12.7 mm.

When the weighting device 10 is implanted in an eyelid 8, the spherical shape of inner surface 13 provides for substantially unrestrained movement of the implant across the surface of the eye when the lid is opened and closed. With the concave surface 13, the inducement of astigmatism is minimized and the implant 10 is more comfortable for the patient as the weight of the implant is not concentrated at the edges of the implant, but is instead evenly distributed across the area of the eye beneath the surface 13. Eyelid closure without induced astigmatism is made more effective by the spherical shape of surface 13, protecting the eye from dryness, irritation and other potentially damaging conditions.

Implant 10 has a pair of spaced, first and second major edges 15 and 16 and a pair of side edges 18 and 19. The first major edge 15 has contoured ends 21 and 22 which, as shown in FIG. 1, are curved upward-outward toward the side edges 18 and 19. The radius of curvature of the contoured ends is preferably in the range of approximately 2 to 3.5 mm. Providing the first major edge 15 with contoured ends reduces the surface area of the inner and outer surfaces 12 and 13 so that the implant is less visible in the eyelid. The first major edge 15 is also tapered as shown in FIG. 3. Reducing the thickness of the implant along the first major edge further lowers the profile of the implant within the lid where the eyelid skin is thinnest. The spherical-shaped implant 10 is less noticeable, a feature that is particularly desirable for the more self-conscious patient. Although in the illustrated embodiment only the first major edge tapered and shaped with contoured ends, it is to be understood that both major edges may be formed with contoured ends and both major edges may be tapered if desired.

The edges 15, 16, 18 and 19 are preferably rounded or smoothed to remove any sharpness and minimize the risk that the implant will extrude through the surface of the lid. Providing the edges of the weighting device 10 with a smooth finish also enhances the comfort of the implant, increasing patient satisfaction.

One or more apertures 24 are formed in the weighting device 10 as shown in FIG. 1. The apertures may be used to anchor the implant 10 to the orbital septum or tarsus, placing it securely parallel to the eyelid margin, depending upon the final placement of the implant in the lid. Sutures may be inserted through one or more of the apertures 24 and fixed to the appropriate tissues. A suture through a second or third aperture may be required to ensure secure placement parallel to the eyelid margin. After time, the placement of the implant 10 is further stabilized by tissue growth through the apertures 24. The number of apertures formed in implant 10 may vary, although three apertures are generally suitable for implants with weights between approximately 0.8 and 1.6 grams, while lighter implants may require only one aperture as shown in FIG. 5. It should be understood that the number of apertures 24 in the weighting device 10 may be increased or decreased as desired.

The implant 10 has a thickness of approximately 0.75 to 1.25 mm, for example 1.0 mm, and a width of approximately 3.5 to 5.5 mm, for example 5.0 min. The nominal length of the implant varies depending upon the weight of the implant (as shown in FIG. 5) and the material from which the implant is fabricated. Suitable materials include gold, tantalum, platinum, or a combination of materials such as gold plated tantalum or platinum. Gold is preferred as it has a high specific gravity (19.21) and the color of the metal blends with the fat in the eyelid, where many silver colored metals are visible through the eyelid. In the illustrated modification the implant 10 has a weight of between 0.6 and 2.8 grams, although the weight of the implant may be increased or decreased as desired.

The weighting device 10 is implanted using the appropriate surgical techniques. The placement of the implant 10 may be septal (FIG. 4A) or pretarsal (FIG. 4B) depending upon the preference of the surgeon and the individual needs of the patient. Septal placement is often preferred as the implant is less conspicuous, although some prefer lower pretarsal placement since the required weight for eyelid closure is reduced. When fixed to the orbital septum, the implant is oriented with the first major edge 15 facing downward as shown particularly in FIG. 4A. The first major edge 15 may face upward, as shown in FIG. 4B, or downward when the implant is secured to the tarsus. Orienting the implant 10 as described ensures that the contoured ends 21 and 22 and the tapered portion of the implant are situated in the thinnest portion of the eyelid.

Another embodiment of an eyelid weighting device in accordance with the invention is shown in FIGS. 6–10. Weighting device 30 has an outer surface 32, a concave inner surface 33, major edges 35 and 36 and side edges 38 and 39. The concave inner surface 33 is shaped to conform to the generally spherical curvature of the globe, and preferably has a radius of curvature in the range of 11.5 to 13.5 mm. The weighting device 30 is not implanted in the lid, but is instead temporarily secured to the exterior of the lid 8. Thus, for optimum comfort the curvature of the concave surface 33 is selected to accommodate the thickness of the eyelid.

Weighting device 30 may be used to determine the weight of an implant required for optimum closure of the eyelid when the levator muscle is relaxed without causing the eyelid to droop excessively when the muscle is contracted. The weighting device 30 is temporarily affixed to the exterior of the eyelid at a central position above the lashes as shown in FIG. 7. After observing the position of the lid when the patient looks up and down, the weighting device is removed and, if necessary, a weighting device 30 having a higher or lower weight is secured to the lid. Once the weighting device having the optimum weight for eyelid closure has been determined, the physician may select the corresponding implant 10 and surgically insert the implant in the eyelid of the patient.

The weighting device 30 is preferably secured to the exterior of the eyelid using an adhesive strip 42 (FIG. 8), although other adhesive means as for example tincture of benzoin, rubber cement, dermatome glue and the like may also be used to affix the device 30 to the lid. The adhesive strip 42 is hypoallergenic and has opposed adhesive surfaces 44 and 45. As shown particularly in FIG. 9, several adhesive strips 42 are attached to an enlarged sheet 47. An elongated top strip 48 is attached to the exposed surface 44 of each strip 42. The top strip 48 is longer than the adhesive strip 42 to provide a flap portion 49 which may be conveniently grasped by the physician and used to pull the top strip 48 and the attached adhesive strip from the enlarged sheet 47. The adhesive surface 45 of the strip 42 is applied to the concave inner surface 33 of the weighting device. With the adhesive strip 42 secured to the device 30, the top strip 48 is removed from the adhesive strip 42 and the adhesive surface 44 affixed to the exterior of the eyelid. If necessary, the weighting device 30 may be removed from the lid and reapplied at a different location. The adhesive strips 42 of the present invention provide an clean, efficient and inexpensive method of temporarily attaching the weighting device to the eyelid.

Using the external weighting device 30 to determine the appropriate weight for the gold implant 10 offers several advantages. The external weighting devices may be used repeatedly by the physician. The weighting device 30 may be used to select the appropriately-sized implant 10 of the previous embodiment or another type of implant as, for example, a cylindrical-shaped implant. Since the weighting devices are not implanted in the eyelid, the devices 30 may be formed of materials other than gold, reducing the cost of the weighting devices. If the physician wishes to determine the appropriate implant weight and insert the implant during the same visit, using separate weighting devices to determine the required implant weight is also more efficient than using the proposed implant, as the implant need not be cleaned of adhesive or sterilized.

The weighting device 30 may be briefly affixed to the eyelid during an office visit to identify the weight required for an implant as is known in the art. Alternatively, in accordance with the present invention, the weighting device may be secured to the exterior of the eyelid for longer periods of time to treat temporary lagophthalmos and to monitor the effect the implant will have on the eyelid. The external eyelid weighting device 30 provides effective treatment for the patient with temporary lagophthalmos. This treatment may be beneficial to the patient who does not wish to receive an implant or who is not treated effectively with other conservative measures. Once the paralysis and lagophthalmos have resolved, the patient may discontinue wearing the external eyelid device.

Securing the weighting device 30 to the lid exterior for extended periods of time, for example several days, also allows the patient to observe first hand that the implant will improve eyelid closure and reduce the irritating and painful effects of exposure of the eye. This is particularly desirable when a patient is nervous about the implantation procedure. Subjecting the lid to the weighting device 30 for extended periods of time also allows the physician to make any necessary adjustments to the implant weight before the implant is inserted in the lid, in some instances eliminating the need for a second procedure.

As shown particularly in FIGS. 6 and 7, the periphery of the weighting device is substantially rectangular in shape. Since the weighting device is secured to the exterior of the eyelid, lowering the profile of the weighting device will not make the device less noticeable. However, the first major edge 35 may be tapered and one or both of the major edges 35 and 36 may be formed with contoured ends if desired. Although the outer surface 32 follows the shape of the concave inner surface 33, the outer surface may be formed in other shapes. As with the previous embodiment, the edges 35, 36, 38 and 39 are preferably rounded or smoothed to reduce the sharpness of the edges. Providing the weighting device 30 with rounded edges enhances the comfort of the device on the eyelid and facilitates handling of the device.

As shown in FIG. 10, the exposed outer surface 32 of the weighting device may be provided with a colored layer 50 if desired. The colored layer 50 may blend with the skin color of the eyelid so that the weighting device 30 is less noticeable. Because of the skin colored coating on the outer surface, the patient will be less self-conscious when the weighting device is affixed to the eyelid for extended periods of time. Alternatively, the colored layer 50 may be coded to correspond to the weight of the weighting device 30, with different colored weighting devices having different weights. Because the weighting devices 30 are generally small in size, the color-coded layers 50 provide a visible and easily discernable indication of the weight of each weighting device. The physician or physician's assistant is no longer required to carefully scrutinize the weighting device to determine the weight of the implant. Thus, with the colored layers 50 the physician may efficiently determine the optimum weight required for improved eyelid closure. Although in the depicted embodiment the exposed outer surface 32 of the weighting device is provided with a colored layer 50, it should be understood that in other modifications of the invention the colored layer may be applied to the lower surface 33. Alternatively, both surfaces 32 and 33 may be coated with a colored layer if desired.

The weighting devices 30 are preferably substantially the same size as the implants 10 to provide a more accurate indication of the effect the implant 10 will have on eyelid closure. However, the thickness, width and length of the weighting device may vary as desired. Preferably, the weighting devices 30 are formed of tantalum, although other materials such as gold, platinum, silver, lead, copper or a combination of materials such as gold plated tantalum may also be used to fabricate the weighting device. It should be understood that the material used to form the devices 30 may require alteration of the dimensions of the weighting device.

As is apparent from the foregoing discussion, the eyelid weighting devices of the present invention provide an efficient system for the treatment of lagophthalmos. The shape of the implants 10 are more comfortable for the patient, offer improved eyelid closure and minimize any effect on visual acuity. The physician may efficiently and accurately determine the optimum weight for eyelid closure with the present invention. Moreover, the eyelid weighting system of the present invention is particularly suitable for treating temporary lagophthalmos resulting from Bell's Palsy with an external weighting device, or for demonstrating the effect the implant will have on the patient's condition before surgery.

What is claimed is:

1. A method of improving the closure of an eyelid comprising the steps of:

selecting a weight body having an outer surface and a concave inner surface having a radius of curvature substantially conforming to the curvature of the eyeball, and attaching said weight body to the exterior of said eyelid with an adhesive substance and leaving said weight body attached thereto for treatment of a medical condition with said weight body facilitating closure of said eyelid during said treatment of said medical condition.

2. The method of claim 1 in which said attaching step includes applying one side of at least one adhesive strip to said inner surface of said weight body and an opposite side of said adhesive strip to said eyelid.

3. The method of claim 1 and further comprising the step of coloring said outer surface of said weight body.

4. The method of claim 3 in which said coloring step includes applying a colored layer to said outer surface, said colored layer being of a color which substantially blends with the color of said eyelid.

5. The method of claim 1 in which said step of selecting a weight body includes providing an eyelid weighting system including a plurality of weight bodies each having a different weight and selecting one of said plurality of weight bodies for said treatment of said medical condition.

* * * * *